(12) United States Patent
Suh et al.

(10) Patent No.: US 7,728,285 B2
(45) Date of Patent: Jun. 1, 2010

(54) PHANTOM DEVICE HAVING INTERNAL ORGAN SIMULATING PHANTOM

(75) Inventors: Tae Suk Suh, Seoul (KR); Jin Beom Chung, Seoul (KR); Jeong Woo Lee, Gyeonggi-Do (KR); Yon Lae, Seoul (KR); Kyoung Sik Choi, Gyeonggi-Do (KR); Jai Sung Kim, Gyeonggi-Do (KR); Kyu Bong Choi, Seoul (KR)

(73) Assignee: Catholic University Industry Academic Cooperation Foundation, Seoul (KR)

( * ) Notice: Subject to any disclaimer, the term of this patent is extended or adjusted under 35 U.S.C. 154(b) by 287 days.

(21) Appl. No.: 11/827,012

(22) Filed: Jul. 9, 2007

(65) Prior Publication Data

US 2008/0011946 A1 Jan. 17, 2008

(30) Foreign Application Priority Data

Jul. 11, 2006 (KR) .................. 10-2006-0064923

(51) Int. Cl.
*G12B 13/00* (2006.01)
*G01N 23/00* (2006.01)
*G01D 18/00* (2006.01)

(52) U.S. Cl. .................. 250/252.1; 378/18; 378/207
(58) Field of Classification Search ............. 250/252.1, 250/363.09, 573, 433, 505.1; 378/18, 207
See application file for complete search history.

(56) References Cited

U.S. PATENT DOCUMENTS 3,764,267 A * 10/1973 Farr et al. .................... 422/81
5,227,627 A * 7/1993 Gamarnik et al. ........ 250/252.1
6,094,760 A * 8/2000 Nonaka et al. ................. 5/601
6,225,622 B1 * 5/2001 Navarro ................... 250/252.1
6,697,451 B2 * 2/2004 Acharya et al. ............... 378/18
2005/0141672 A1 * 6/2005 Endo et al. .................. 378/207
2005/0211889 A1 * 9/2005 Varchena et al. ......... 250/252.1

FOREIGN PATENT DOCUMENTS

KR 1020050074013 A 7/2005
KR 20-0403375 12/2005

* cited by examiner

*Primary Examiner*—David P Porta
*Assistant Examiner*—Faye Boosalis
(74) *Attorney, Agent, or Firm*—Nixon Peabody LLP (57) ABSTRACT

Provided is a phantom device having an internal organ simulating phantom. The phantom device comprises: a phantom receiving radiation emitted from a radiation emitting unit and comprising therein a simulant that simulates an internal organ; a lifting unit installed under the phantom to support the phantom and moving the phantom relative to the radiation emitting unit, the lifting unit comprising: a worm shaft axially rotated by an external torque and having a worm formed on an outer circumferential surface thereof, a cylindrical worm wheel having gear grooves formed on an outer circumferential surface thereof to engage with the worm and a female screw formed on an inner circumferential surface thereof, and rotated by the axial rotation of the worm shaft; and a driven screw engaging with the female screw of the worm wheel, and moved up and down by the rotation of the worm wheel to move up and down the phantom; and a horizontal moving unit interlocking with the lifting unit and horizontally moving the phantom. Accordingly, since the phantom device can simulate any movement pattern, even the respiratory movement pattern of a patient's internal organ to accurately determine a desired dose of radiation to be delivered to the body part, high quality assurance of radiation therapy equipment can be achieved and therapeutic effect can be improved.

14 Claims, 10 Drawing Sheets

PHANTOM DEVICE HAVING INTERNAL ORGAN SIMULATING PHANTOM

CROSS-REFERENCE TO RELATED PATENT APPLICATION

This application claims the benefit of Korean Patent Application No. 10-2006-0064923, filed on Jul. 11, 2006, in the Korean Intellectual Property Office, the disclosure of which is incorporated herein in its entirety by reference.

BACKGROUND OF THE INVENTION

1. Field of the Invention

The present invention relates to a phantom device having an internal organ simulating phantom.

2. Description of the Related Art

Among various uses of radiation, medical radiation therapy is used to kill cancer cells or alleviate pain for a patient suffering from cancer by emitting radiation to a tumor and preventing the tumor from growing.

In particular, radiation therapy is very useful when cancer cells remain after surgery and there is a high risk of cancer recurrence, when surgery cannot be practiced, when radiation therapy is more effective than surgery, when a combination of surgery and radiation therapy improves the quality of life for a cancer patient, or when a combination of drug treatment and radiation therapy maximizes anticancer effect.

Meantime, radiation therapy is performed by means of expensive medical equipment called a linear accelerator. Since the linear accelerator cannot only output high-dose-rate X-rays and electron beams but also can finely adjust output energy, it is currently used as standard equipment for radiation therapy.

It is essential to radiation therapy that the linear accelerator outputs radiation of appropriate energy. Since radiation conforming to the grade, size, or depth of a tumor results in maximum treatment effect, it is very important to enable the linear accelerator to produce optimal energy radiation.

As such, before using the linear accelerator, it is necessary to check whether the linear accelerator can operate normally and, in particular, can emit radiation at desired energy levels after radiation dose adjustment. This process, called quality assurance, is performed in hospitals periodically or non-periodically.

Various dosimetric systems are used for quality assurance. In principle, a dosimetric system is located under a radiation emitting unit to receive radiation emitted by the radiation emitting unit, and generates and outputs signals corresponding to the radiation. Since optimal radiation appropriate for a patient's tumor cannot be measured without the dosimetric system, an optimal dose of radiation cannot be delivered to the tumor, thereby reducing therapeutic anticancer effect and even causing medical malpractice in cases of excessive radiation exposure.

Conventional dosimetric systems can measure the dose of radiation while being fixed within a radiation path, but disadvantageously cannot move, for example, in repetitive patterns of internal organs of the human body which move according to respiration.

Accordingly, whether accurate or not, information about radiation dosage is obtained from a fixed target, not from a moving one. Since there is a difference between a dose administered to a moving target and a dose administered to a fixed target, it is somewhat difficult to use this information as data for quality assurance of radiation therapy equipment that is to be used to emit radiation to the target moving according to respiration.

As described above, in order to emit appropriate energy radiation to a moving target in a patient's body, that is, to enable the linear accelerator to deliver an accurate dose of radiation to the moving target, quality assurance should be performed by using a phantom simulating the dynamics of the moving target. However, a device that can precisely move a phantom in desired patterns has not yet been developed.

SUMMARY OF THE INVENTION

The present invention provides a phantom device having a phantom that can simulate any movement pattern, even the respiratory movement pattern of a patient's internal organ to accurately determine a desired dose of radiation to be delivered to the internal organ, thereby achieving high quality assurance of radiation therapy equipment and improving therapeutic effect.

According to an aspect of the present invention, there is provided a phantom device having an internal organ simulating phantom, the phantom device comprising: a phantom receiving radiation emitted from a radiation emitting unit and comprising therein a simulant that simulates an internal organ; a lifting unit installed under the phantom to support the phantom and moving the phantom relative to the radiation emitting unit, the lifting unit comprising: a worm shaft axially rotated by an external torque and having a worm formed on an outer circumferential surface thereof; a cylindrical worm wheel having gear grooves formed on an outer circumferential surface thereof to engage with the worm and a female screw formed on an inner circumferential surface thereof, and rotated by the axial rotation of the worm shaft; and a driven screw engaging with the female screw of the worm wheel, and moved up and down by the rotation of the worm wheel to move up and down the phantom; and a horizontal moving unit interlocking with the lifting unit and horizontally moving the phantom.

The lifting unit and the horizontal moving unit may be disposed on a horizontal surface of a base plate. The driven screw engaging with the worm wheel may extend over the worm wheel and a lifting member may be fixed to an upper end of the driven screw. A lift guide member may be disposed between the lifting member and the base plate to guide the lifting movement of the lifting member relative to the base plate and support the driven screw by means of the lifting member.

A first plate having a horizontal surface may be disposed on the lifting member. The horizontal moving unit may comprise: a motor mounted on the first plate; a first driven member horizontally and linearly reciprocated by the motor mounted on the first plate; a second plate connected to the first driven member and linearly reciprocated along the driven member; a motor mounted on the second plate; a second driven member linearly reciprocated by the motor in a direction perpendicular to the reciprocating direction of the first driven member; and a phantom fixing plate coupled to the second driven member to be reciprocated along the second driven member, and allowing the phantom to be fixed to a top surface thereof.

A lead screw may be connected to the shaft of each of the motors to be axially rotated by the motor. Each of the first and second driven members may be a driven block that engages with the lead screw and is linearly moved in a longitudinal direction of the lead screw by the axial rotation of the lead screw.

The phantom device may further comprise phantom fixing means disposed on the phantom fixing plate to fix the phantom to the phantom fixing plate.

The phantom fixing means may comprise: support walls fixed to the top surface of the phantom fixing plate and supporting one or more pixels of the phantom; and a phantom fixing unit pressing the phantom against the support walls and fixing the phantom to the phantom fixing plate.

The phantom may comprise a phantom body made of acryl and having therein a space simulating the shape of the internal organ.

The phantom may further comprise a simulant inserted into the space of the phantom body and simulating the internal organ.

The phantom body may be formed by stacking a plurality of acrylic slabs each having a predetermined width.

Dosimeter grooves into which dosimeters for measuring the dose of radiation are inserted may be formed in some of the slabs constituting the phantom.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

The present invention will now be described more fully with reference to the accompanying drawings, in which exemplary embodiments of the invention are shown.

Figure 1:
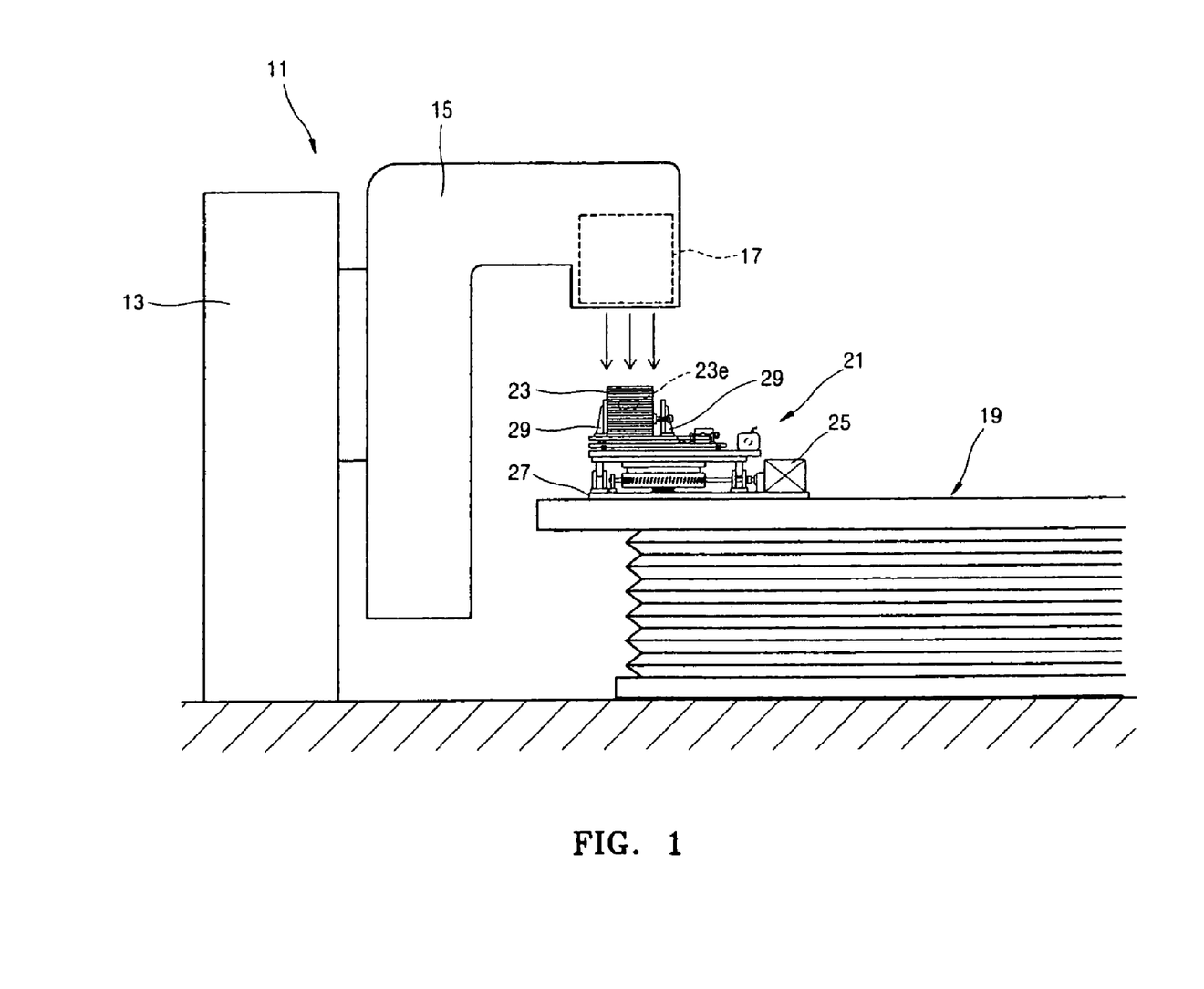
FIG. 1 is a side view of a phantom device which is applied to a linear accelerator and having an internal organ simulating phantom according to an embodiment of the present invention.

FIG. 1 is a side view of a phantom device 21 which is applied to a linear accelerator 11 and having an internal organ simulating phantom 23 according to an embodiment of the present invention.

Referring to FIG. 1, the phantom device 21 is placed on a horizontal bed 19. The bed 19, which forms a set with the linear accelerator 11, is a horizontal table on which a patient lies down.

The linear accelerator 11 includes a body 13 and a gantry 15 rotating relative to the body 13. A high voltage generator or a microwave generator is installed in the body 13, and an accelerating tube for accelerating electrons, a magnetic field generator, and a radiation emitting unit 17 are installed in the gantry 15. Radiation output from the radiation emitting unit 17 is emitted to a tumor of the patient lying on the bed 19.

The phantom device 21 having the phantom 23, which is placed on the bed 19 and located below the radiation emitting unit 17, receives radiation emitted from the radiation emitting unit 17. The radiation output from the radiation emitting unit 17 is emitted to the phantom 23 of the phantom device 21 to detect the dose of the emitted radiation.

In particular, while the radiation is emitted from the radiation emitting unit 17, the phantom 23 is moved back and forth, left and right, and up and down by first through third motors which will be explained later. The phantom 23 is designed to resemble the movement pattern of a target body part of the patient.

Consequently, the dose and distribution of radiation to be emitted to the target body part, i.e., the tumor, of the patient can be determined in advance by measuring the dose of radiation emitted to a simulant 23e inside the phantom 23 that is moved in all directions. In order to measure the dose of radiation, a dose detector should be first located in the phantom 23. A thermoluminescent dosimeter or a metal oxide semiconductor field effect transistor (MOSFET) dosimeter or film may be used as the dose detector.

Figure 2:
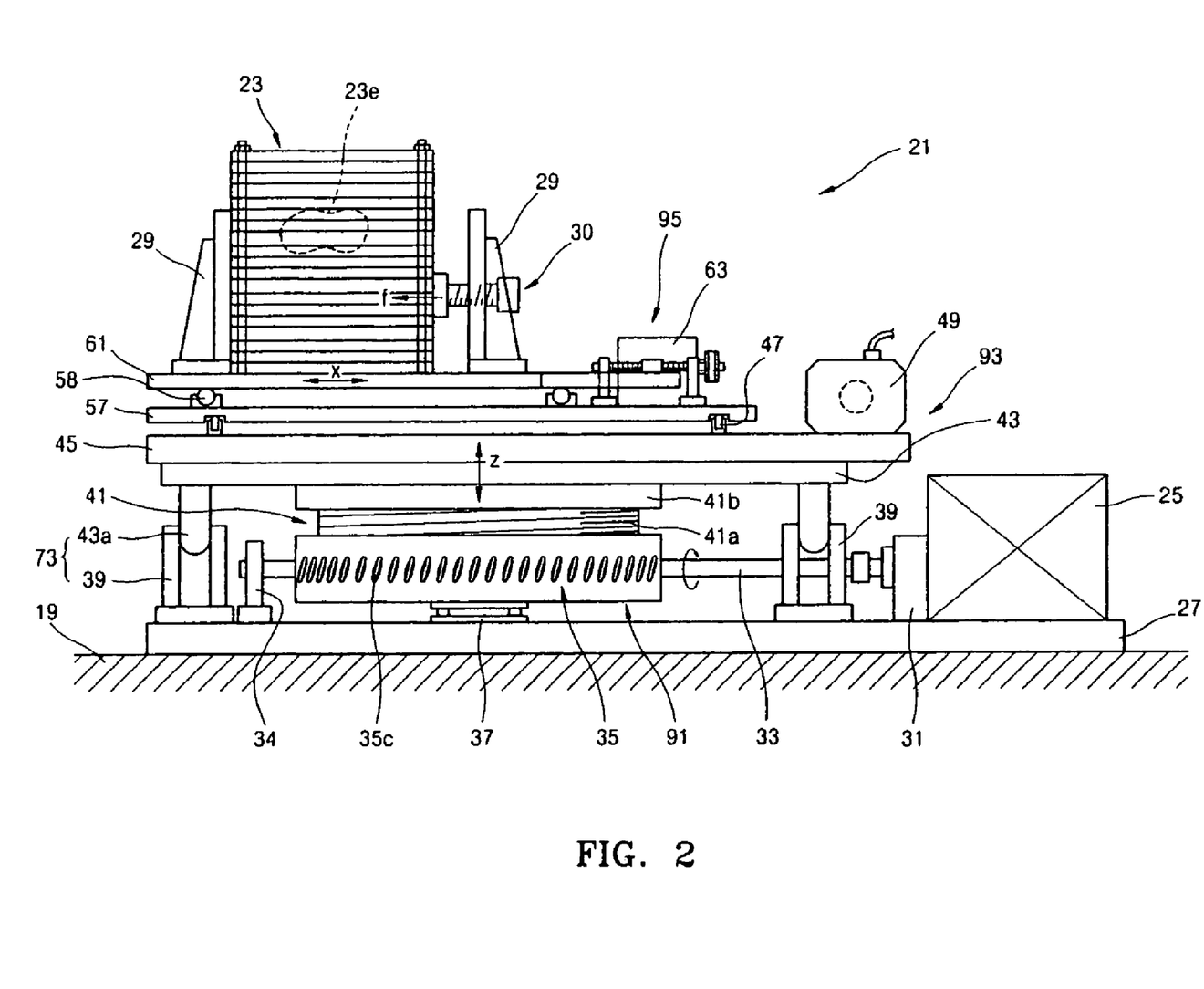
FIG. 2 is a side view of the phantom device of FIG. 1, according to an embodiment of the present invention.

FIG. 2 is a side view illustrating the entire structure of the phantom device 21 having the phantom 23 of FIG. 1, according to an embodiment of the present invention.

Referring to FIG. 2, the phantom device 21 includes a base plate 27 placed on a flat die, e.g., the bed 19 (see FIG. 1), and having a horizontal support surface, a Z-direction driving unit 91 installed over the base plate 27 and providing a Z-direction force, a Y-direction driving unit 93 installed over the Z-direction driving unit 91 and reciprocating in a Y direction (see FIG. 5), an X-direction driving unit 95 installed over the Y-direction driving unit 93 and reciprocating in an X direction, and the phantom 23 mounted on the X-direction driving unit 95. A controller 25 is disposed on the base plate 27 to control the movement pattern of the phantom 23.

The X-, Y-, and Z-direction driving units 95, 93, and 91 three-dimensionally move the phantom 23 relative to the radiation emitting unit 17, such that the phantom 23 can be moved in the same movement pattern as that of the target body part of the patient.

The Z-direction driving unit 91 includes a first motor 31 fixed to a side of the base plate 27, a worm shaft 33 axially rotated by the first motor 31 and having a worm 33a (see FIG. 3) formed on an outer circumferential surface thereof, a cylindrical worm wheel 35 disposed on a side of the worm shaft 33 and having a plurality of gear grooves 35c formed on an outer circumferential surface thereof and a female screw 35d (see FIG. 3) formed on an inner circumferential surface thereof, a driven screw 41 extending upward and engaging with the female screw 35d of the worm wheel 35, a lifting plate 43 fixed to an upper end of the driven screw 41 and kept parallel to the base plate 27, and a lift guide member 73 disposed between the base plate 27 and the lifting plate 43.

The lift guide member 73 guides the lifting movement of the lifting plate 43 and prevents the lifting plate 43 from being rotated. The lift guide member 73 includes cylindrical vertical guiders 39 fixed to the base plate 27 and having open upper ends, and guide rods 43*a* mounted on a bottom surface of the lifting plate 43 and partially inserted into the vertical guiders 39 to guide the lifting movement of the lifting plate 43. A bearing 37 rotatably supports the worm wheel 35.

The Z-direction driving unit 91 will be explained later with reference to FIGS. 3 and 4.

A first plate 45 is disposed on the lifting plate 43. The first plate 45 has a horizontal surface large enough to support the Y-direction driving unit 93. If the lifting plate 43 is large enough to support the Y-direction driving unit 93, the first plate 43 may be omitted.

The Y-direction driving unit 93 includes a second motor 49 installed on the first plate 45, a lead screw 51 (see FIG. 5) axially rotated by the second motor 49, and a driven block 53 fixed to the second plate 57 by engaging with the lead screw 51, and linearly moved in a Y direction by the axial rotation of the lead screw 51 to reciprocate the second plate 57 in the Y direction.

A plurality of bearings 47 fixed to the first plate 45 are disposed under the second plate 57 and guide the movement of the second plate 57 relative to the first plate 45. A plurality of bearings 58 are also disposed on the second plate 57 to horizontally support a phantom fixing plate 61 and guide the phantom fixing plate 61 in an X direction. The Y-direction driving unit 93 will be explained again with reference to FIG. 5.

Figure 6:
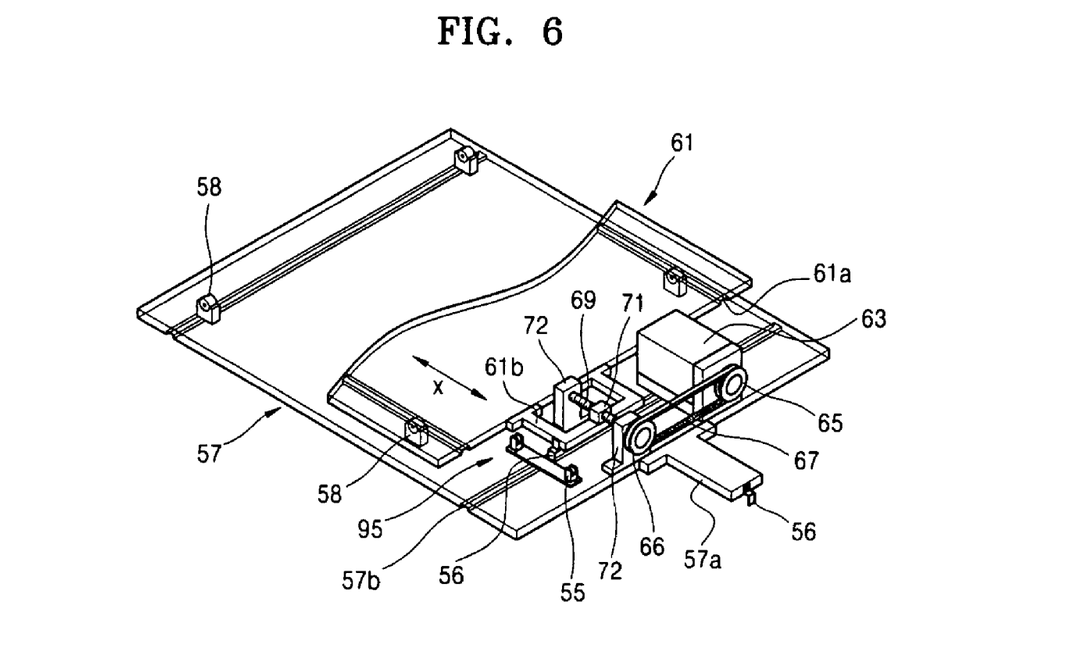
FIG. 6 is a partially cutaway perspective view for explaining the drive mechanism of a phantom fixing plate of the phantom device of FIG. 2, according to an embodiment of the present invention.

The X-direction driving unit 95 includes a third motor 63 fixed to the second plate 57, and the phantom fixing plate 61 is reciprocated in an X direction by the third motor 63. The X-direction driving unit 95 has a construction as shown in FIG. 6 and will be explained later with reference to FIG. 6.

The phantom 23 is disposed on the phantom fixing plate 61, and fixing means for firmly fixing the phantom 23 to a top surface of the phantom fixing plate 61 is provided. The fixing means includes two support walls 29 facing each other with the phantom 23 therebetween, and a phantom fixing unit 30 passing through one of the two support walls 29 and pressing the phantom 23 in an "f" direction.

The phantom 23 installed on the phantom fixing plate 61 is formed by stacking a plurality of acrylic slabs, and includes the simulant 23*e* therein. The simulant 23*e* can simulate an internal organ, such as lung, liver, heart, or stomach, of the human body, which moves according to respiration.

Figure 3:
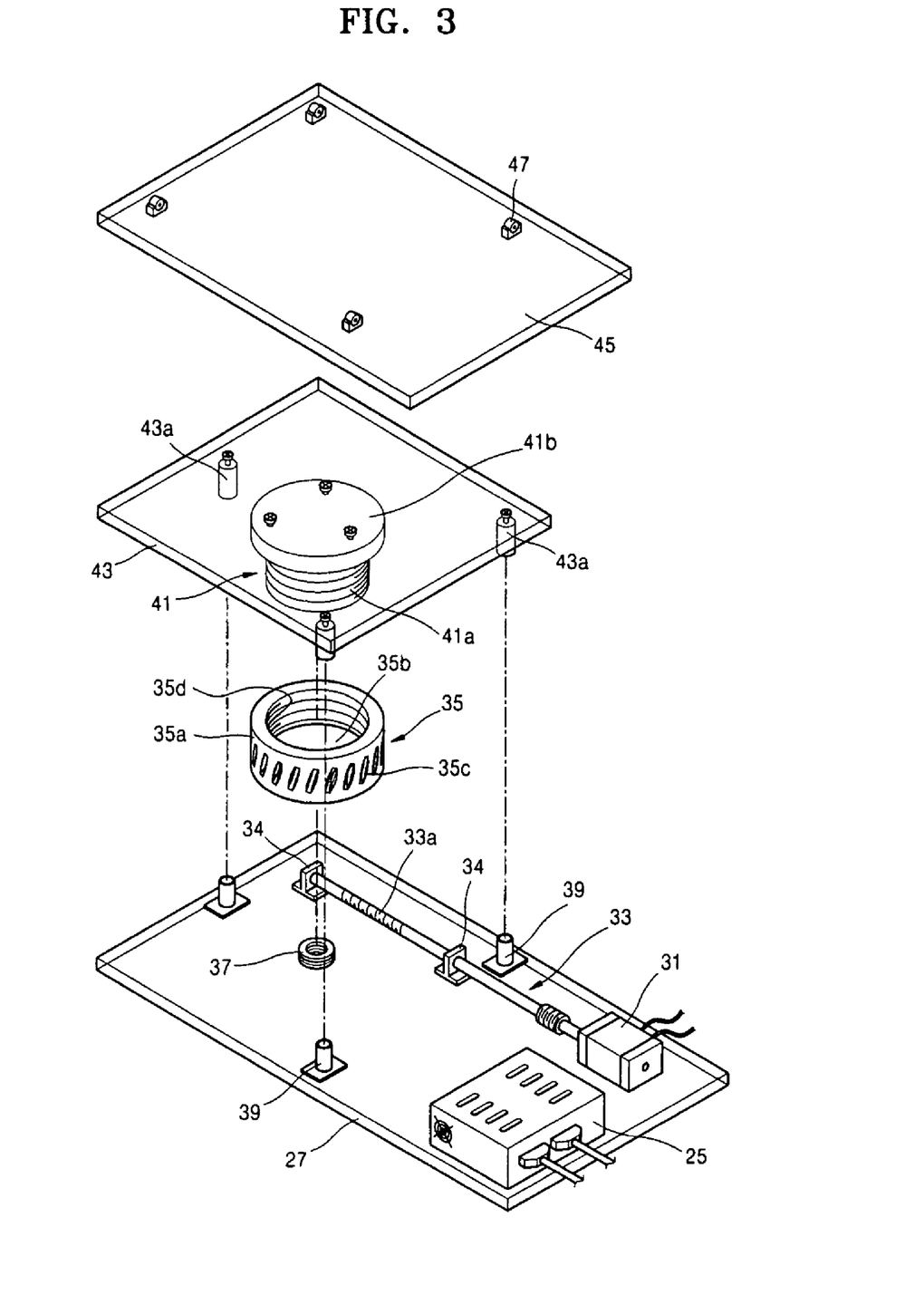
FIG. 3 is a partially exploded perspective view of the phantom device of FIG. 2, according to an embodiment of the present invention.
Figure 4:
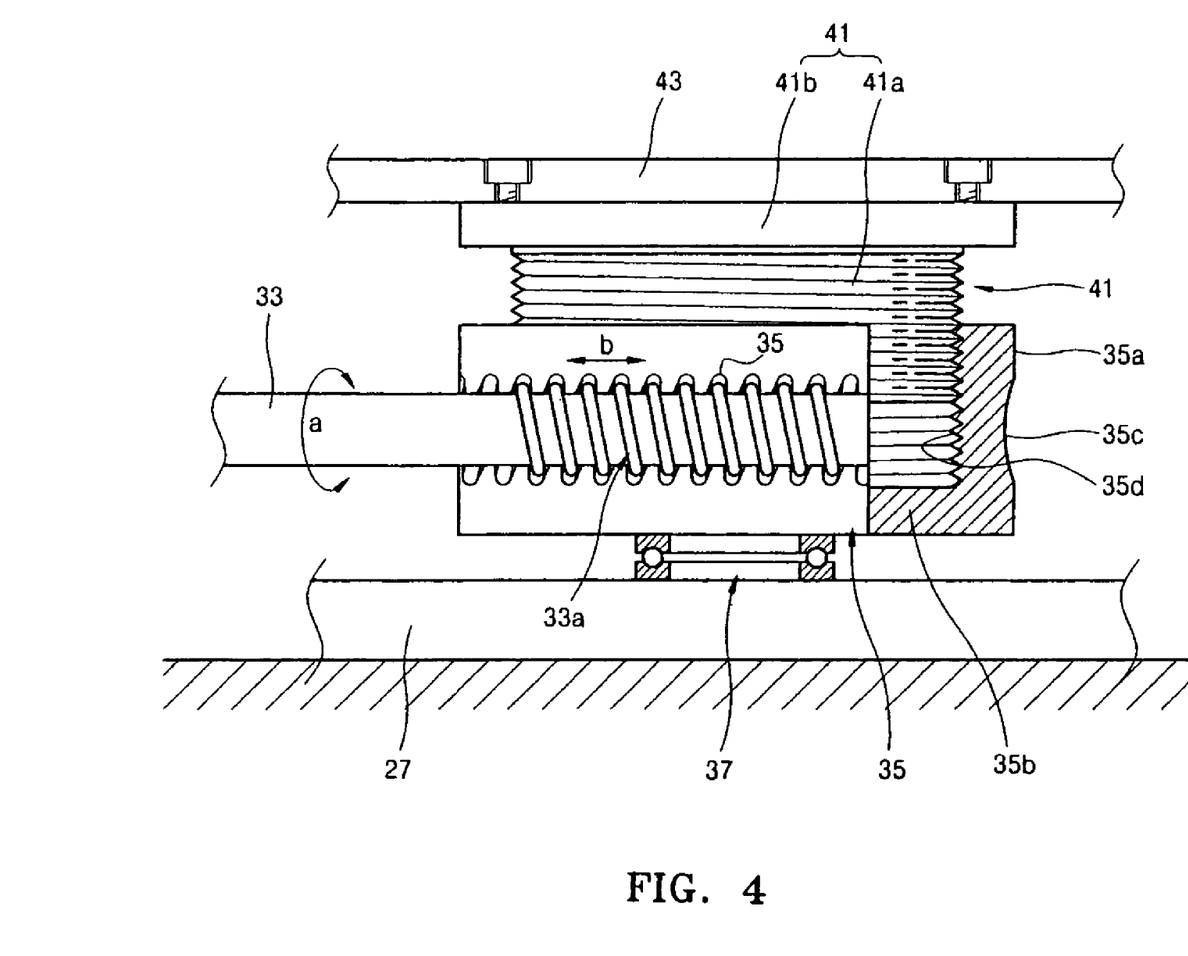
FIG. 4 is a side view of the phantom device of FIG. 3 when assembled, according to an embodiment of the present invention.

FIGS. 3 and 4 are an exploded perspective view and a side view, respectively, illustrating the Z-direction driving unit 91 of the phantom device 21 of FIG. 2. according to embodiments of the present invention.

Referring to FIGS. 3 and 4, the first motor 31 is disposed on a side of a top surface of the base plate 27, and the worm shaft 33 is connected to the shaft of the first motor 31. The worm shaft 33 is horizontally supported by a plurality of shaft supports 34 and is axially rotated by the torque of the first motor 31. The worm shaft 33 is made of synthetic resin or engineering plastic.

The worm 33*a* formed on the worm shaft 33 has helical gear teeth formed thereon such that the helical gear teeth engage with the gear grooves 35*c* formed on the outer circumferential surface of the worm wheel 35.

The bearing 37 is disposed beside the worm 33*a*. The bearing 37 is a thrust bearing that rotatably supports the worm wheel 35. The bearing 37 and the worm wheel 35 should be concentric.

The worm wheel 35 disposed on the bearing 37 has a sidewall 35*a* and a bottom 35*b*, and has a cylindrical shape open at an upper end thereof. The bottom 35*b* is fixed to the bearing 37 to be horizontally supported. The sidewall 35*a* with a predetermined thickness has the gear grooves 35*c* and the female screw 35*d* respectively formed on the outer and inner circumferential surfaces thereof.

The gear grooves 35*c* engage with the worm 33*a*, and when the worm shaft 33 is axially rotated in an "a" direction, are rotated in a "b" direction to move up and down the driven screw 41.

The driven screw 41 meshes with the worm wheel 35. The driven screw 41 includes a male screw 41*a* partially engaging with the female screw 35*d* and a fixing part 41*b* having a predetermined thickness and integrally formed with an upper end of the male screw 41*a*. The fixing part 41*b* is coupled to the square lifting plate 43. The lifting plate 43, which is an acrylic plate having a predetermined thickness, horizontally and fixedly supports the driven screw 41 and moves up and down the first plate 45 according to the movement of the driven screw 41.

Three vertical guiders 39 are installed around the worm wheel 35. The vertical guiders 39 are vertical pipe-shaped members into which the vertical guide rods 43*a* are inserted to guide the lifting movement of the lifting plate 43 and prevent the lifting plate 43 from being rotated.

The guide rods 43*a* are annular rods fixed to the bottom surface of the lifting plate 43 and vertically and downwardly extending from the bottom surface of the lifting plate 43, and correspond to the vertical guiders 39 in a one-to-one manner. The guide rods 43*a* partially inserted into the vertical guiders 39 as shown in FIG. 2 are vertically driven simultaneously with the movement of the lifting plate 43 to prevent the lifting plate 43 from being shaken or rotated.

The first plate 45 is closely fixed to the top of the lifting plate 43. The first plate 45, which is a square acrylic plate having a predetermined thickness, has a horizontal surface on which the plurality of bearings 47 are disposed. The Y-direction driving unit 93 is disposed on the first plate 45.

Figure 5:
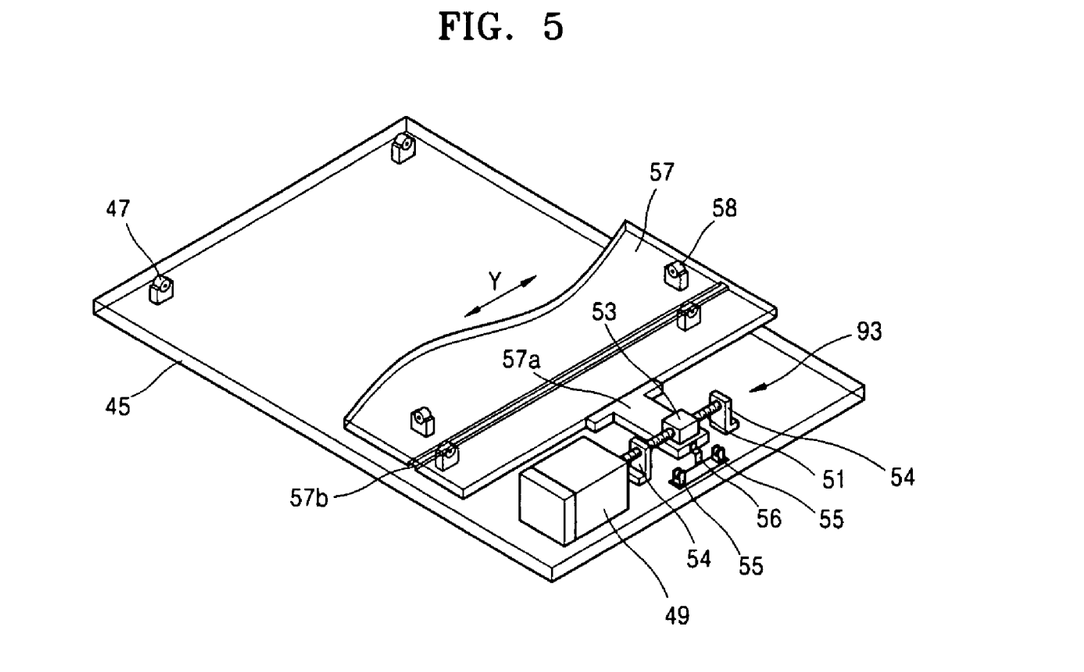
FIG. 5 is a partially cutaway perspective view for explaining the drive mechanism of a second plate of the phantom device of FIG. 2, according to an embodiment of the present invention.

FIG. 5 is a perspective view for explaining the mechanism of driving the second plate 57 by means of the Y-direction driving unit 93 of FIG. 2, according to an embodiment of the present invention.

Referring to FIG. 5, the Y-direction driving unit 93 is disposed on a side of a top surface of the first plate 45. The Y-direction driving unit 93 horizontally moves the second plate 57 in a Y direction.

The Y-direction driving unit 93 includes the second motor 49 fixed to a side on a top surface of the first plate 45, the lead screw 51 horizontally extending to be connected to the shaft of the second motor 49 and having both ends supported by supporters 54, and the driven block 53 allowing the lead screw 51 to pass therethrough and reciprocated in a longitudinal direction of the lead screw 51 by the axial rotation of the lead screw 51.

The driven block 53 is fixed to a protrusion 57*a* of the second plate 57. The protrusion 57*a* is fixed to an end of the second plate 57, and extends toward the lead screw 51 to be coupled to the driven block 53 to transmit the movement force of the driven block 53 to the second plate 57.

The bearings 47 fixed to the top surface of the first plate 45 are inserted into bearing grooves 57*b* having predetermined widths and depths. The bearings 47 whose upper ends are inserted into the bearing grooves 57b support horizontally the second plate 57 such that the second plate 57 can be smoothly moved in the Y direction.

The plurality of bearings 58 mounted on the second plate 57 support the phantom fixing plate 61 horizontally (see FIG. 6), and guide the phantom fixing plate 61 in an X direction.

A metal piece 56 is disposed on a front end of the protrusion 57a, and two sensors 55 are disposed on both sides under the metal piece 56. The sensors 55 are spaced by a predetermined distance from each other, and sense the movement distance of the metal piece 56.

Each of the sensors 55 generates a signal when the metal piece 56 passes through the sensor 55. Accordingly, when the metal piece 56 moved along the driven block 53 reaches one of the sensors 25, the sensor 55 generates a signal to the controller 25 to indicate that the metal piece 56 has reached the sensor 55. Next, the controller 25 reversibly rotates the second motor 49 to move the driven block 53 in the opposite direction. The sensing mechanism is well known.

The sensors 55 of the Y-direction driving unit 93 determine the maximum Y-direction reciprocating distance of the second plate 57. Accordingly, the maximum Y-direction stroke of the second plate 57 can be increased by increasing the distance between the sensors 55.

In practice, however, the metal piece 56 is reciprocated between the sensors 55 without reaching the sensors 55. The stroke of the metal piece 56, that is, the stroke of the driven block 53, is controlled by the controller 25.

FIG. 6 is a detailed perspective view for explaining the mechanism of driving the phantom fixing plate 61 by means of the X-direction driving unit 95, according to an embodiment of the present invention. The X-direction driving unit 95 horizontally moves the phantom fixing plate 61 in an X direction.

Referring to FIG. 6, the X-direction driving unit 95 includes the third motor 63 disposed on a side of a top surface of the second plate 57, a lead screw 69 axially rotated by the torque of the third motor 63, and a driven block 71 allowing the lead screw 69 to pass therethrough and be reciprocated by the axial rotation of the lead screw 69.

The driven block 71 is coupled to a C-shaped projection 61b fixed to an end of the phantom fixing plate 61. The lead screw 69 is parallel to the shaft of the third motor 63 and has both ends horizontally supported by supporters 72.

In order to transmit the torque of the third motor 63 to the lead screw 69, a driving pulley 65 is mounted on the shaft of the third motor 63, a driven pulley 66 is mounted on an end of the lead screw 69, and the driving pulley 65 and the driven pulley 66 are connected to each other via a belt 67. Accordingly, the torque of the third motor 63 can be transmitted to the lead screw 69 via the belt 67.

The driven block 71 is reciprocated in a longitudinal direction of the lead screw 69 by the axial rotation of the lead screw 69, and reciprocates the phantom fixing plate 61 in an X direction by means of the projection 61b fixed to the bottom thereof. The phantom fixing plate 61 horizontally supported by the bearings 58 disposed on the second plate 57 is reciprocated within a predetermined range.

A plurality of bearing grooves 61a into which upper ends of the bearings 58 are inserted are disposed on the phantom fixing plate 61 such that the phantom fixing plate 61 can be linearly moved. The bearing grooves 61 a having predetermined widths and depths are parallel to one another.

In order to limit the maximum movement distance of the phantom fixing plate 61, a metal piece 56 is disposed on an end of the projection 61b and a pair of sensors 55 are installed under the metal piece 56. The operating principles of the metal piece 56 and the sensors 55 are the same as described with reference to FIG. 5.

Figure 7:
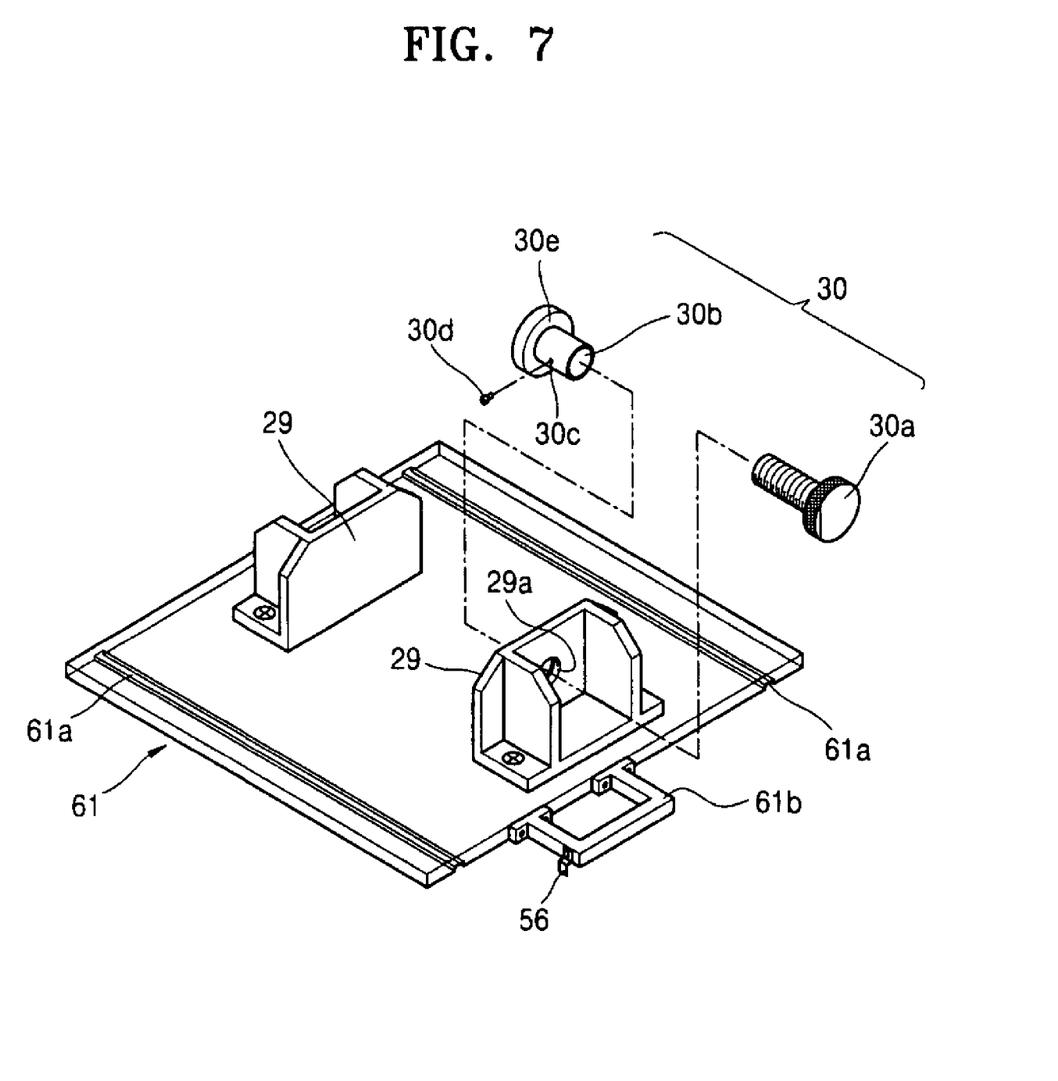
FIG. 7 is a perspective view illustrating a phantom fixing plate and support walls of the phantom device of FIG. 2, according to an embodiment of the present invention.

FIG. 7 is a perspective view illustrating the phantom fixing plate 61 and the support walls 29 of the phantom device of FIG. 2, according to an embodiment of the present invention.

Referring to FIG. 7, the pair of support walls 29 are disposed at both sides on the top surface of the phantom fixing plate 61. The support walls 29 face each other to be spaced apart by a predetermined distance, and firmly press the phantom 23 (see FIG. 2) disposed therebetween as shown in FIG. 2. The support walls 29 and the phantom fixing unit 30 are made of acryl. The number and structure of the support walls 29 are not limited to the present embodiment.

The phantom fixing unit 30 is disposed on one of the support walls 29. A female screw hole 29a into which a pressing screw 30a of the phantom fixing unit 30 is inserted is formed in the support wall 29.

The phantom fixing unit 30 includes the pressing screw 30a inserted into the female screw hole 29a, a cylindrical screw connection 30b into which an end of the pressing screw 30a is fixedly inserted, and a disk-shaped support plate 30e integrally formed with the screw connection 30b.

A front end of the pressing screw 30a inserted into the screw connection 30b is fixed by a fixing screw 30d. A female screw hole 30c into which the fixing screw 30d is inserted is formed in a sidewall of the screw connection 30b.

Figure 8:
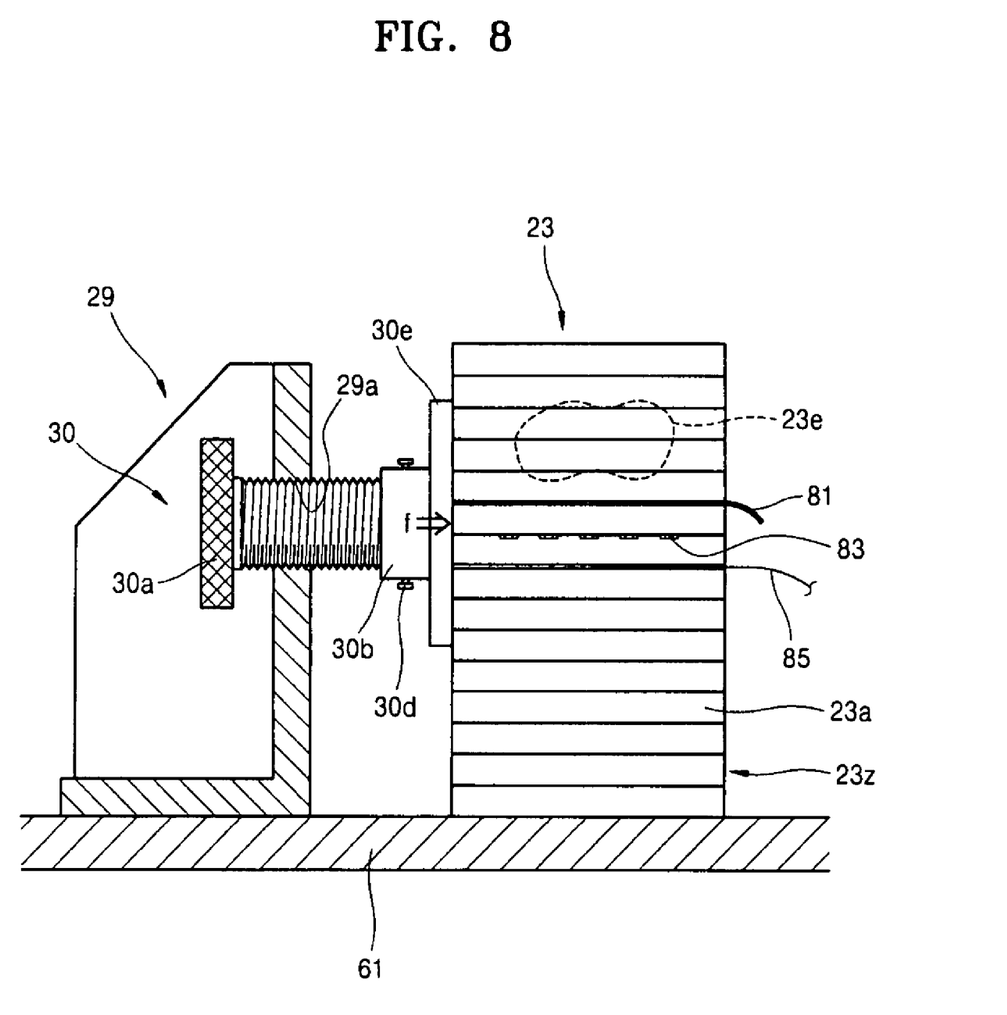
FIG. 8 is a side view for explaining the operating principle of a phantom fixing unit of the phantom device of FIG. 7, according to an embodiment of the present invention.

FIG. 8 is a side view for explaining the operating principle of the phantom fixing unit 30 of FIG. 7, according to an embodiment of the present invention.

Referring to FIG. 8, the phantom 23 can be pressed in an "f" direction by rotating the pressing screw 30a of the phantom fixing unit 30 mounted on one of the support walls 29.

The phantom 23 mounted on the phantom fixing plate 61 is formed by stacking a plurality of unit slabs 23a. The structure of the phantom 23 will be explained in detail with reference to FIG. 9.

Figure 9:
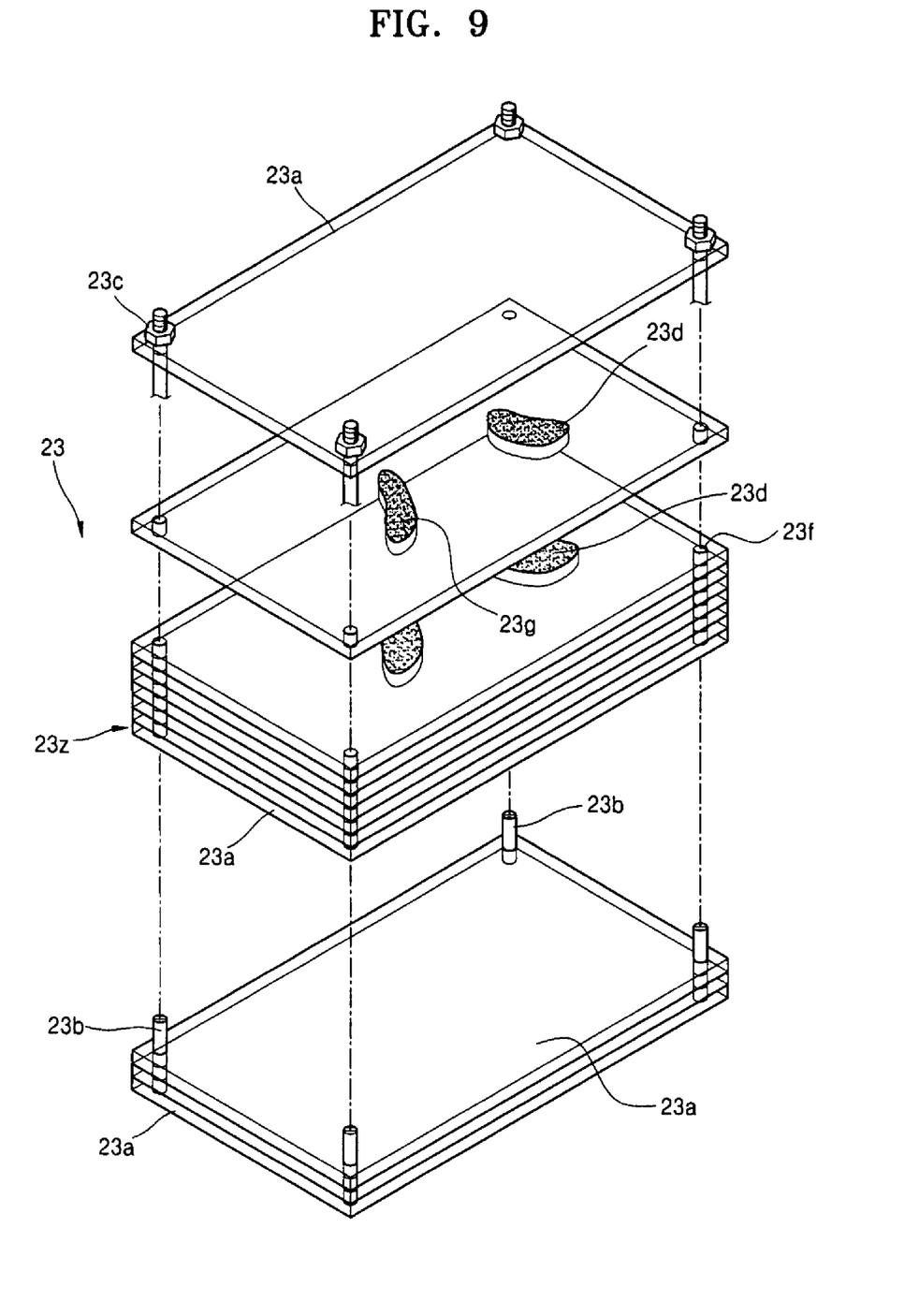
FIG. 9 is a partially exploded perspective view illustrating the phantom of the phantom device of FIG. 2, according to an embodiment of the present invention.
Figure 10:
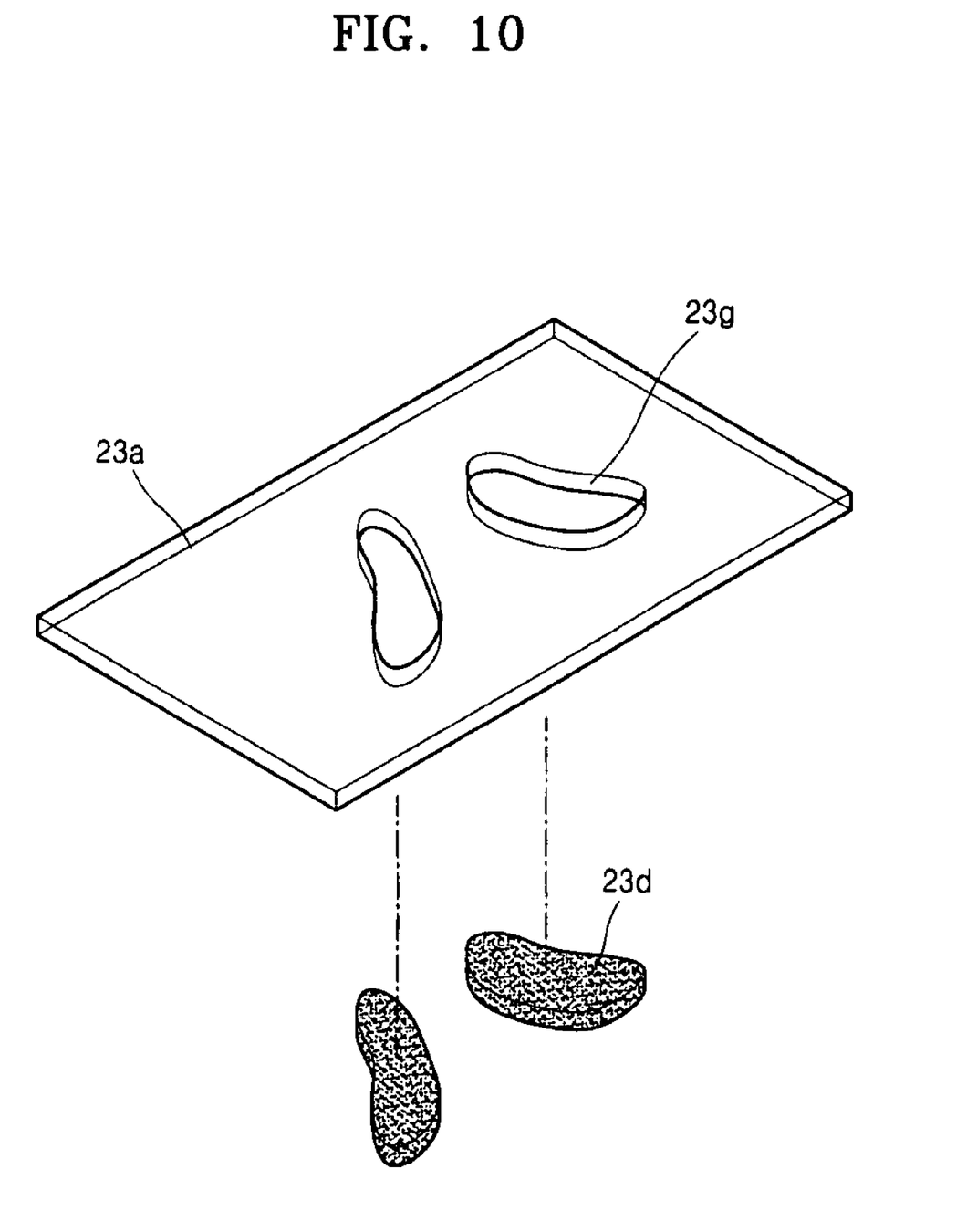
FIG. 10 is a partially exploded perspective view of the phantom of FIG. 9, according to an embodiment of the present invention.

FIG. 9 is a partially exploded perspective view of the phantom 23 of FIG. 2, and FIG. 10 is an exploded perspective view illustrating any one of the unit slabs 23a constituting a phantom body 23z of the phantom 23 of FIG. 9, according to embodiments of the present invention.

The phantom 23 formed by stacking the plurality of slabs 23a includes the phantom body 23z having therein a space that simulates the shape of an internal organ, and the simulant 23e located in the space inside the phantom body 23z.

Each of the slabs 23a constituting the phantom body 23z has a predetermined thickness and is made of acryl. Section holes 23g are formed in some slabs 23a as illustrated in FIG. 10. The section holes 23g are through-holes representing outlines of the cross-section of the internal organ.

That is, the section holes 23g represent images of the internal organ tomographed at intervals in a direction from the back to the chest. Accordingly, the section holes 23g have different shapes for different slabs 23a, and the shape of the internal organ can be embodied by sequentially stacking the slabs 23a.

Referring to FIG. 9, the plurality of slabs 23a are sequentially stacked to form one phantom 23. Each of the slabs 23a is rectangular and has through-holes 23f formed in four corners thereof.

The through-holes 23f permit vertical rods 23b to pass therethrough. The vertical rods 23b upwardly pass through the through-holes 23f of the stack of slabs 23a and upper ends of the vertical rods 23b are coupled to nuts 23c to vertically fasten the slabs 23a to one another.

In particular, a film 81 (see FIG. 8) may be inserted into the stack of slabs 23a fixed by the nuts 23c as shown in FIG. 8 by loosening the nuts 23c and slightly lifting the slabs 23a. The film 81 is used to detect the dose of radiation passing through the simulant 23e.

Simulant pieces 23d are inserted into the section holes 23g of the slabs 23a. The simulant pieces 23d are automatically stacked when the slabs 23a are sequentially stacked, so as to form one simulant 23e.

The simulant 23e is made of a tissue-equivalent material for a simulated subject. For example, a simulant 23e simulating a lung is made of cork since the density of cork is almost equivalent to that of the lung.

The simulant 23e is made of a proper material according to the kind of a simulated internal organ. The simulant pieces 23d may be made of acryl similarly to the slabs 23a, or teflon or paraffin.

The simulant pieces 23d are inserted into the section holes 23g, the slabs 23a are stacked, and radiation is emitted to the phantom 23 in a thickness direction of the simulant pieces 23d. As a result, the energy level of radiation at a target depth can be obtained and radiation treatment planning can be conducted based on the energy level.

Figure 11:
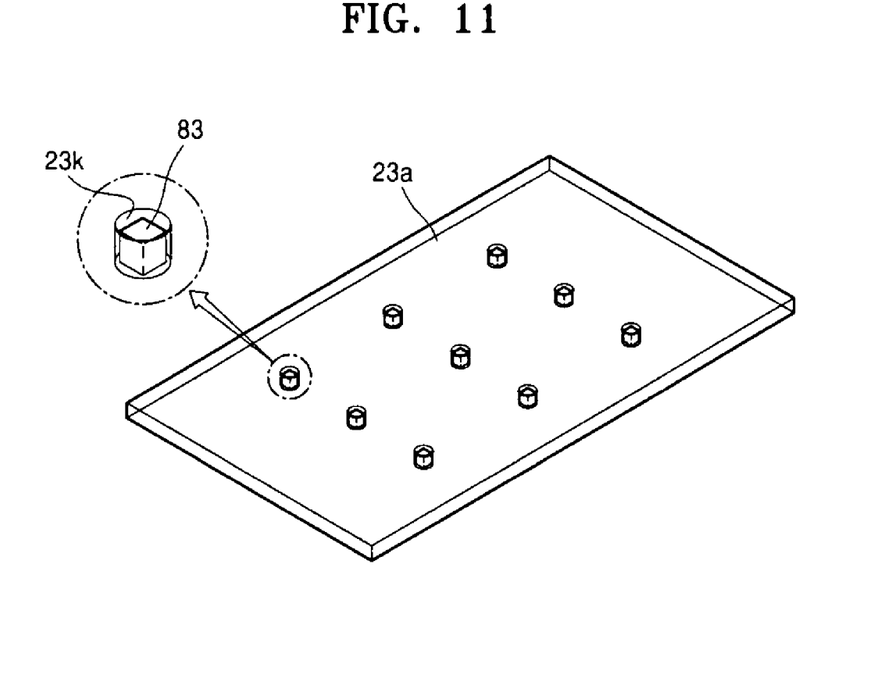
FIGS. 11 and 12 are perspective views illustrating slabs of the phantom of FIG. 9, according to an embodiment of the present invention.
Figure 12:
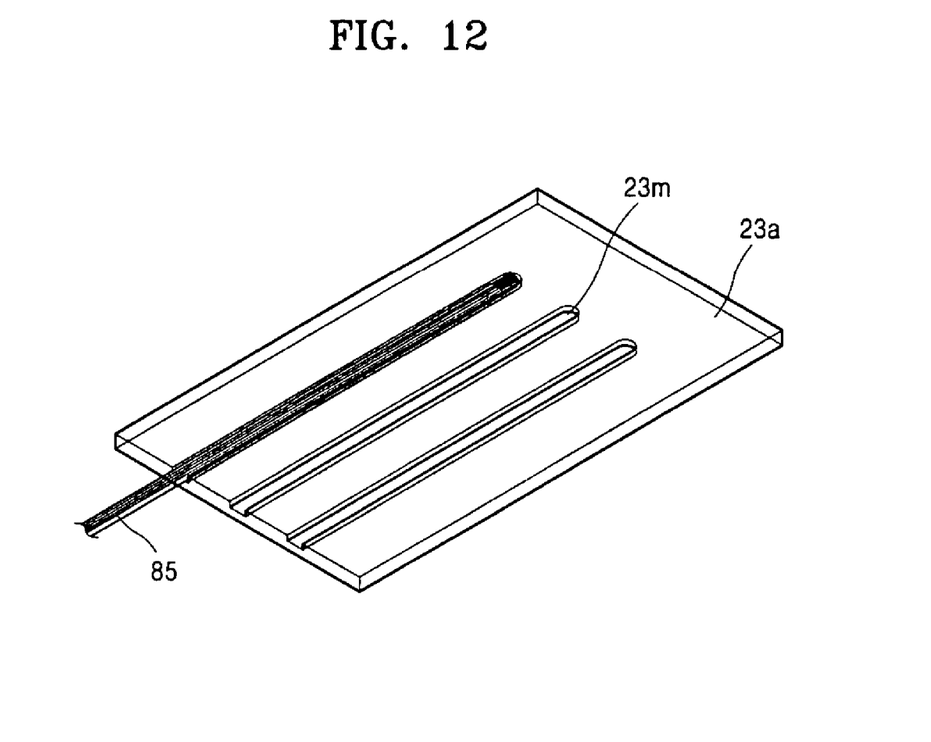

FIGS. 11 and 12 are perspective views illustrating some slabs 23a of the phantom 23 of FIG. 9, according to embodiments of the present invention. The slabs 23 illustrated in FIGS. 11 and 12 are disposed under the simulant 23e as illustrated in FIG. 8.

Referring to FIG. 11, a plurality of dosimeter grooves 23k are formed in a top surface of a slab 23a, according to an embodiment of the present invention. The dosimeter grooves 23k are arranged at predetermined intervals and allow thermoluminescent dosimeters 83 to be inserted thereinto. Since the slab 23a on which the thermoluminescent dosimeters 83 are installed is disposed under the simulant 23e as illustrated in FIG. 8, the dose of radiation under the simulant 23e can be obtained.

Referring to FIG. 12, a plurality of dosimeter grooves 23m extend longitudinally in a slab 23a, according to an embodiment of the present invention. The plurality of dosimeter grooves 23m are parallel to one another, and allow MOSFET dosimeters to be inserted thereinto. Accordingly, since the slab 23a on which the MOSFET dosimeters 85 are installed is disposed under the simulant 23e as illustrated in FIG. 8, the dose of radiation under the simulant 23e can be obtained.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A phantom device having an internal organ simulating phantom, the phantom device comprising:
    a phantom receiving radiation emitted from a radiation emitting unit and comprising therein a simulant that simulates an internal organ;
    a lifting unit installed under the phantom to support the phantom and moving the phantom relative to the radiation emitting unit while the phantom receives the radiation, the lifting unit comprising:
        a worm shaft axially rotated by an external torque and having a worm formed on an outer circumferential surface thereof;
        a cylindrical worm wheel having gear grooves formed on an outer circumferential surface thereof to engage with the worm and a female screw formed on an inner circumferential surface thereof, and rotated by the axial rotation of the worm shaft; and
        a driven screw engaging with the female screw of the worm wheel, and moved up and down by the rotation of the worm wheel to move up and down the phantom; and
    a horizontal moving unit interlocking with the lifting unit and horizontally moving the phantom.

2. The phantom device of claim 1, wherein the lifting unit and the horizontal moving unit are disposed on a horizontal surface of a base plate,
    wherein the driven screw engaging with the worm wheel extends over the worm wheel and a lifting member is fixed to an upper end of the driven screw,
    wherein a lift guide member is disposed between the lifting member and the base plate to guide the lifting movement of the lifting member relative to the base plate and support the driven screw by means of the lifting member.

3. The phantom device of claim 2, wherein a first plate having a horizontal surface is disposed on the lifting member,
    wherein the horizontal moving unit comprises:
    a motor mounted on the first plate;
    a first driven member horizontally and linearly reciprocated by the motor mounted on the first plate;
    a second plate connected to the first driven member and linearly reciprocated along the driven member;
    a motor mounted on the second plate;
    a second driven member linearly reciprocated by the motor in a direction perpendicular to the reciprocating direction of the first driven member; and
    a phantom fixing plate coupled to the second driven member to be reciprocated along the second driven member, and allowing the phantom to be fixed to a top surface thereof.

4. The phantom device of claim 3, wherein a lead screw is connected to the shaft of each of the motors to be axially rotated by the motor,
    wherein each of the first and second driven members is a driven block that engages with the lead screw and is linearly moved in a longitudinal direction of the lead screw by the axial rotation of the lead screw.

5. The phantom device of claim 3, further comprising phantom fixing means disposed on the phantom fixing plate to fix the phantom to the phantom fixing plate.

6. The phantom device of claim 5, wherein the phantom fixing means comprises:
    support walls fixed to the top surface of the phantom fixing plate and supporting one or more pixels of the phantom; and
    a phantom fixing unit pressing the phantom against the support walls and fixing the phantom to the phantom fixing plate.

7. The phantom device of claim 1, wherein the phantom comprises a phantom body made of acryl and having therein a space simulating the shape of the internal organ.

8. The phantom device of claim 7, wherein the phantom further comprises a simulant inserted into the space of the phantom body and simulating the internal organ.

9. The phantom device of claim 8, wherein the phantom body is formed by stacking a plurality of acrylic slabs each having a predetermined width.

10. The phantom device of claim 9, wherein dosimeter grooves into which dosimeters for measuring the dose of radiation are inserted are formed in some of the slabs constituting the phantom.

11. The phantom device of claim 1, wherein the horizontal moving unit moves the phantom along a horizontal direction while the phantom receives the radiation.

12. The phantom device of claim 1, wherein the phantom is moved back and forth along one or more desired directions while receiving the radiation.

13. A phantom device having an internal organ simulating phantom, the phantom device comprising:
- a phantom receiving radiation emitted from a radiation emitting unit and comprising therein a simulant that simulates an internal organ;
- a lifting unit installed under the phantom to support the phantom and moving the phantom relative to the radiation emitting unit in a vertical direction while the phantom receives the radiation; and
- a horizontal moving unit interlocking with the lifting unit and horizontally moving the phantom while the phantom receives the radiation.

14. The phantom device of claim 13, wherein the lifting unit further comprises: a worm shaft axially rotated by an external torque and having a worm formed on an outer circumferential surface thereof;
- a cylindrical worm wheel having gear grooves formed on an outer circumferential surface thereof to engage with the worm and a female screw formed on an inner circumferential surface thereof, and rotated by the axial rotation of the worm shaft; and
- a driven screw engaging with the female screw of the worm wheel, and moved up and down by the rotation of the worm wheel to move up and down the phantom.

* * * * *